(12) United States Patent
Bader

(10) Patent No.: US 7,388,507 B2
(45) Date of Patent: Jun. 17, 2008

(54) SYSTEM AND METHOD FOR REGISTERING THE TEMPERATURE OF A PERSON

(76) Inventor: Gaby Bader, Lilla Danska Vägen 12, Göteborg (SE) S-412 74

( * ) Notice: Subject to any disclaimer, the term of this patent is extended or adjusted under 35 U.S.C. 154(b) by 158 days.

(21) Appl. No.: 10/544,351

(22) PCT Filed: Feb. 2, 2004

(86) PCT No.: PCT/SE2004/000137

§ 371 (c)(1),
(2), (4) Date: Oct. 3, 2005

(87) PCT Pub. No.: WO2004/069048

PCT Pub. Date: Aug. 19, 2004

(65) Prior Publication Data

US 2006/0139165 A1   Jun. 29, 2006

(30) Foreign Application Priority Data

Feb. 3, 2003   (SE) .................................... 0300278

(51) Int. Cl.
*G08B 23/00* (2006.01)
(52) U.S. Cl. ................ 340/573.1; 340/584; 340/673.5; 340/825.36; 340/825.49
(58) Field of Classification Search ............ 340/573.1, 340/584, 673.5, 825.36, 825.49
See application file for complete search history.

(56) References Cited

U.S. PATENT DOCUMENTS 6,198,394 B1 * 3/2001 Jacobsen et al. ......... 340/573.1

FOREIGN PATENT DOCUMENTS

| DE | 19812518 A1 | 9/1999 |
| EP | 0 757 907 A1 | 2/1999 |
| GB | 2329022 A | 3/1999 |
| JP | 08140808 A | 6/1996 |
| WO | WO 01/64103 A1 | 9/2001 |
| WO | WO 01/95848 A2 | 12/2001 |

OTHER PUBLICATIONS

International Search Report of PCT/SE2004/000137, mailed Apr. 30, 2004.

* cited by examiner

*Primary Examiner*—Daryl C Pope
(74) *Attorney, Agent, or Firm*—Potomac Patent Group PLLC

(57) ABSTRACT

A system and method for registering the temperature of a person, wherein a textile product, intended to abut against the person during use, is provided with a number of temperature sensors and a registration unit for registering measurement values from the sensors. The system may be used for monitoring the state of a person, wherein a predetermined threshold condition is monitored, and an alarm signal is emitted to activate an alarm unit when the condition is fulfilled. The system may also be used for controlling physical characteristics of a foundation, such as temperature and/or hardness, based on the state of a person being present thereon.

17 Claims, 2 Drawing Sheets

SYSTEM AND METHOD FOR REGISTERING THE TEMPERATURE OF A PERSON

TECHNICAL FIELD

The present invention relates to a system and method for registering the temperature in a textile product included in a cushion, mattress or garment against which a person is present.

BACKGROUND OF THE INVENTION

In certain cases, it is necessary to detect the temperature of a person, in particular changes of temperature. For example, a bedridden person having a fever should be watched in order to take actions if the temperature of the person becomes too high, i.e. exceeds a certain threshold value. For example, anxious parents feel the need to "take the temperature" frequently on their ill small children when having a fever, to find out how the illness develops. In reverse, it is desirable to monitor whether the temperature of a person suffering from hypothermia falls below a certain threshold value. Further, it may be of interest to detect and analyse the variations in temperature of a person during a period of time. For example, such information may be used to make a diagnosis of a patient, or estimate the sleep quality or general state of a person, whether he/she is ill or well.

Temperature monitoring is typically performed by applying one or more thermometers, or temperature sensors generally, at the person in question, typically using a wired connection to some separate registering unit, for automatic registration and possibly processing and analysis of measurement values from the thermometer. Of course, such a solution will result in some degree of inconvenience to the person carrying such a thermometer at or inside the body, as well as the risk that the thermometer comes off or for some reason does not work properly. Alternatively, the temperature is manually measured at frequent instances, which is labour-intensive, however, in particular when the person must be monitored continuously. Thus, it is a problem to be able to register the temperature of a person, using a minimum of labour, in a reliable way and without bothering the person.

Another area of interest is the comfort for lying or sitting persons. For example, it is a problem to maintain just the right temperature which is comfortable for a person lying in a bed or the like. Lying injuries or bedsores may also occur on persons who for some reason remain bedridden and relatively motionless during long periods of time due to, e.g., physical injury, disease, disablement or high age. Further, it may generally be uncomfortable to lie or sit down for long periods, particularly in the same position, often resulting in stiffness and numbness. Hence, there is a need to be able to control the temperature and also further characteristics in a bed or seat where a person is present, in order to provide a high convenience and to avoid discomfort and injuries.

SUMMARY OF THE INVENTION

It is an object of the present invention to provide registration of the temperature of a person, without requiring that a thermometer is applied on or in the person's body.

It is another object of the present invention to obtain a solution providing a high convenience to a lying or sitting person being present on a foundation.

These objects and others are obtained by a system and method for registering the temperature of a person according to the attached claims. The invented system comprises a textile product intended to abut against the person during use, and being provided with a plurality of temperature sensors arranged to continuously measure the temperature of the person. The system further comprises a registration unit for registering measurement values from the temperature sensors. In different applications, the textile product may be included in a mattress, cushion or garment.

According to different aspects of the invention, the invented system may be used in a procedure of monitoring the state of a person, wherein a predetermined threshold condition is monitored, and an alarm signal is emitted to activate an alarm unit when the condition is fulfilled. The invented system may also be used in a procedure of controlling at least one physical characteristic of a foundation, such as the temperature and/or hardness, based on the state of a person being present thereon.

BRIEF DESCRIPTION OF THE DRAWINGS

The present invention will now be described in more detail by means of a preferred exemplary embodiment and with reference to the accompanying drawings, in which.

DETAILED DESCRIPTION OF EMBODIMENTS

Figure 1:
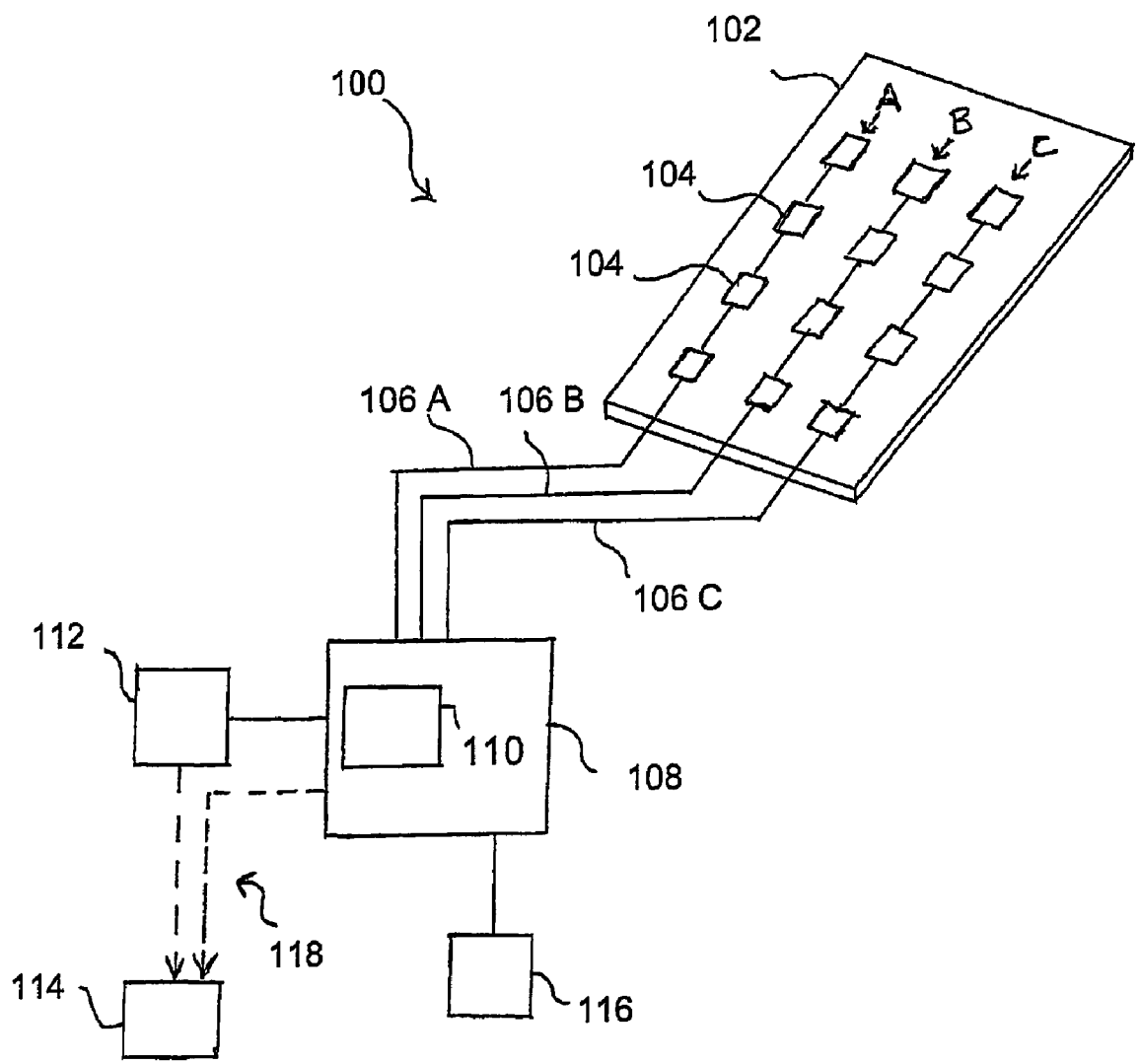
FIG. 1 is a schematic perspective view of a system for registering the temperature of a person.

In FIG. 1, a system 100 is schematically shown for registering the temperature of a person, comprising a textile product 102 intended to abut against the person during use. Here, the term textile product is intended to be construed in a rather broad sense. Thus, the textile product 102 can be made for different applications and may for example be included in a mattress or cushion upon which the person is lying or sitting during use, or in a garment carried by the person. The textile product may further be made in any material suitable for the application, such as a fabric material. These different applications have in common the fact that, in use, the textile product substantially abuts against the person's body, which is necessary for this invention. In the textile product 102, a number of temperature sensors 104 are provided to continuously measure the temperature of the person. The invention is not limited to any particular kind of temperature sensors, but they may be optionally selected among those available on the market. According to different embodiments of the invention, the measured temperature is then used in different ways, which is further described below. The sensors are mounted in the textile product, preferably positioned in a pattern providing an adequate measurement of the person's temperature. The sensors may then be appropriately positioned as a matrix, which facilitates analysis of the spatial temperature distribution, e.g. by using a corresponding system of coordinates.

In the example shown in FIG. 1, the sensors 104 are connected to a registration unit 108 by means of cables 106A-C, for registration of measurement values therefrom. Here, the sensors are connected in three groups A-C, where group A is connected with cable 106A, group B is connected with cable 106B, and group C is connected with cable 106C. Of course, the number of sensors and groups may also be optionally selected, within the scope of the invention. Hence, each sensor group together with its associated cable connection form a measurement circuit having sensors connected in series, such that measurement values from the individual sensors in the group can be read sequentially, which in itself is a well-known technique in the field of measuring. It is also possible to connect one or more sensors directly to the registration unit 108 by means of a cable of its own. However, connection in groups is preferable if a great number of sensors are used, since the number of cables then can be reduced. For example, in certain practical applications, a hundred sensors may be used.

According to another possible alternative, the temperature sensors may be provided with transmitters for wireless transfer of measurement values to a receiver at the registration unit 108, not shown. In that case, the transmitters and the receiver may be produced to utilise some suitable technique for wireless transmission, such as IR-technique or radio, e.g. according to the Bluetooth standard.

In a possible implementation with sensor groups, each connected in a measurement circuit, the system can be arranged in a known manner per se, using a registration unit as a "master" and sensors as "slaves", where each sensor connected to the measurement circuit has been assigned its own address code. When the master shall write to or read from a specific slave, a call including the unique address code is first sent to the slave which is thereby activated to receive a command from the master, whereas the other slaves in the circuit remain passive. After a certain period of time, this command is followed by data for writing, or data is collected for reading. All is done by means of the same physical cable running between all units. As a result, the master can send out a call, and after a predetermined clock period, listen to data from the selected slave, i.e. in this case, a measurement value. Thus, since also a voltage can be output to the sensors by means of this data signal, only one earth wire and one data signal wire are needed to establish the measurement circuit.

Figure 2:
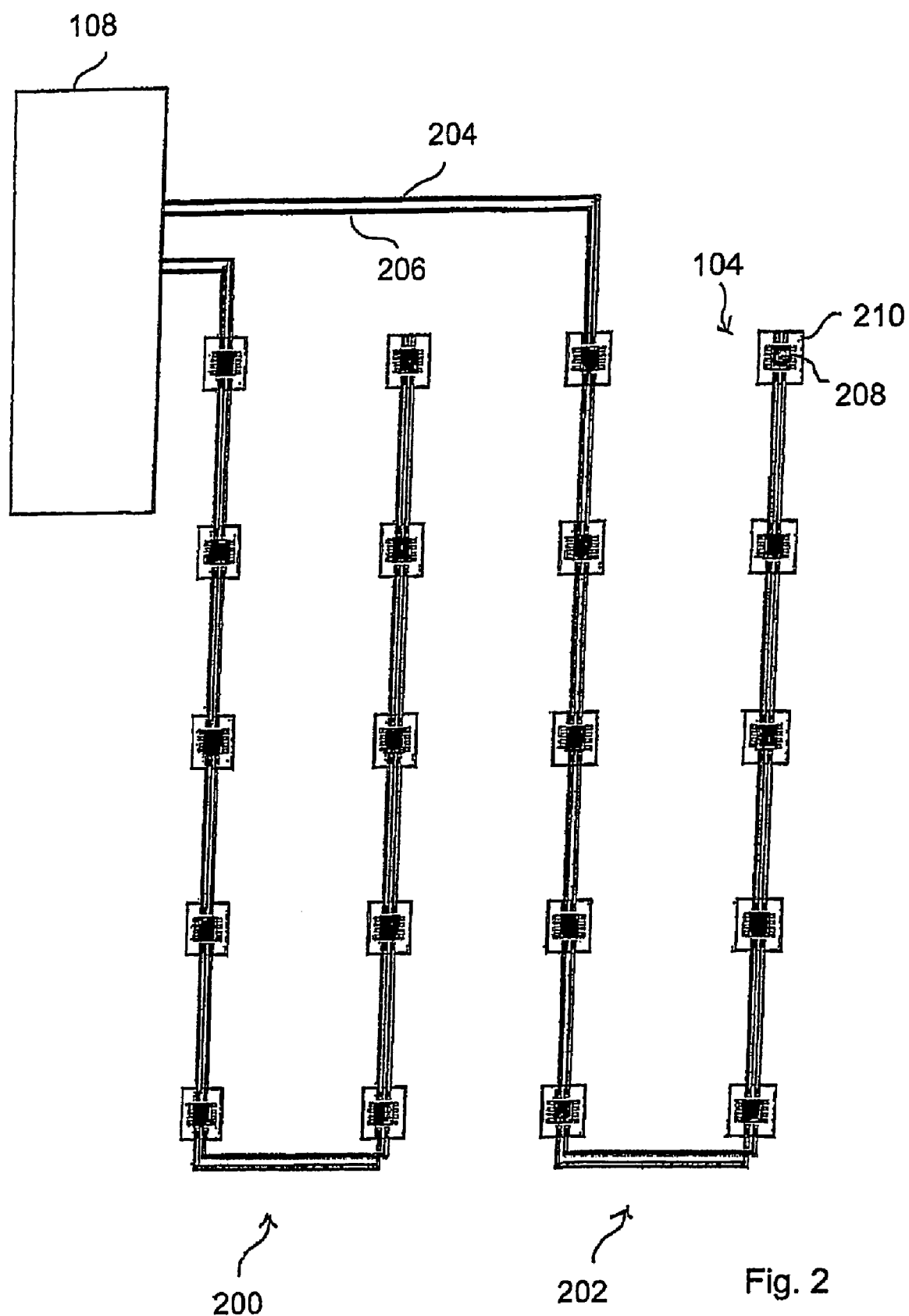
FIG. 2 is a more detailed view of an exemplary embodiment of a system having plural temperature sensors.

FIG. 2 illustrates in more detail a possible embodiment of two such sensor groups 200, 202, each having ten temperature sensors 104 positioned to form a matrix. In this embodiment, each connection cable 106 includes two parallel wires 204, 206 connected to the registration unit 108. Furthermore, each sensor 104 comprises a measurement circuit 208, e.g. in the form of a chip, mounted on a circuit board 210. In a practical exemplary embodiment, the dimensions of the circuit board 210 can be selected having a length 11 mm, width 9 mm and thickness 2.5 mm.

It should be noted that the present invention is not limited to any particular arrangement or specific components to convey measurement values of the temperature from sensors to the registration unit, but the above-described embodiments provide only possible examples.

Returning to FIG. 1, the registration unit 108 comprises a programmable processor 110 for receiving and handling measurement values from the sensors. In this example, the registration unit 108 is further connected, to a separate computer unit 112, such as a PC, which may be provided with various applications for processing and analysing the measurement values received from the sensors 104, and for presenting or accounting for measurement results to a user of the system 100. Alternatively, the functionality for such processing and analysing of measurement values may be programmed directly into the processor 110, such that results therefrom can be obtained directly from the registration unit 108.

For example, the registration unit 108 or the computer unit 112 may thus be adapted to calculate various parameters describing the temperature distribution over a surface covered by the sensors, i.e. spatial information, and how it has changed over a period of time, i.e. temporal information. Various charts, diagrams, tables, etc. may also be created in order to illustrate this.

An alarm unit 114 may also be connected to the registration unit 108 or to the computer unit 112, as indicated with dashed lines in the figure, in order to emit an alarm if a predetermined threshold condition is fulfilled, such as a light signal or a sound signal. For example, such a threshold condition may be that the temperature from a certain number of sensors exceeds a given value during a predetermined period of time. The processor 110 or the computer unit 112 may be programmed to monitor the threshold condition and emit an alarm signal 118, in order to activate the alarm unit 114 when the condition is fulfilled. In FIG. 1, a power source 116 is also schematically shown, which may be, e.g., a battery or a transformer connected to the public power supply network.

As a complement to the above-described temperature measuring, one or more moisture sensors may also be arranged in the textile product, not shown, in order to register perspiration of the person, which may provide important information for estimating the state of the person.

As mentioned above, obtained measurement results can then be used in different ways. According to one embodiment, the measurement results are used for monitoring the state of the observed person. The measurement results may thus provide an indication regarding, e.g., a state of disease of a patient, the sleep quality or general state, which can be used to make a diagnosis. The measurement results may further be used to trigger an alarm when a predetermined threshold condition is fulfilled. This condition may then be selected to indicate whether the state of the patient has developed in a way that requires some action, such as examination or medication.

According to another embodiment, the measurement results are used to control one or more physical characteristics of a foundation in which the above described textile product is included, based on the state of a person being present thereon. For example, the temperature in a mattress may be controlled after the measured temperature of the person, and optionally also based on registered perspirations when moisture sensors are used, in order to obtain a high convenience. Such a mattress is then provided with equipment for temperature regulation, such as cooling and/or heating coils suitably adapted to this object, which is not described further here.

The measurement results may also be used for analysing the pressure distribution in a lying or sitting surface when a person is present thereon. An excessive temperature at a certain spot or small area on the textile product during a certain time period may be an indication of an excessive pressure as compared to the remaining surface. This may give rise to discomfort to the person, such as stiffness and numbness, and in unfavourable cases, may result in surface strain injuries, such as bedsores. According to a specific embodiment, this information is utilised to change the hardness of the surface by means of a suitable mechanism, in response to the excessive temperature, such that the pressure is relieved in that spot. Today, mechanisms are available for varying the hardness or contact pressure in mattresses. Such known techniques may thus be used in the above described manner in the present invention. This application is primarily useful for persons being disabled due to, e.g., a disease, high age, paralysis or physical injury, but also to increase the lying or sitting comfort in general.

According to yet another embodiment, the textile product is included in a garment to be carried by an observed person, and the measurement results are used to estimate the state of the person, e.g. during ongoing work.

It should be noted that in the above described applications, it is of primary interest to register relative changes of the temperature, and how they occur spatially and temporarily. By means of the present invention, a flexible and reliable solution is obtained to, with a minimum of effort, register the temperature of a person without in any way bothering him/her.

The invention is not limited to the described embodiments, but is generally defined by the following claims.

The invention claimed is:

1. A system for registering the temperature of a person, comprising:
   a textile product intended to abut against the person during use, and being provided with a plurality of temperature sensors arranged to continuously measure the temperature of the person,
   a registration unit for registering measurement values from the temperature sensors,
   wherein the temperature sensors are positioned in the textile product so as to form a matrix,
   and further wherein at least one of: the registration unit and a computer unit connected thereto, is adapted to calculate:
   (a) at least one spatial information parameter describing a distribution of a temperature over a surface covered by the sensors using a corresponding system of coordinates for analysing spatial temperature distribution, and
   (b) at least one temporal information parameter describing how said distribution of temperature has chanced during a period of time.

2. A system according to claim 1, further comprising that at least some of the temperature sensors are connected in groups to the registration unit, wherein each sensor group together with an associated cable connection form a measurement circuit with sensors connected in series, for sequential reading of measurement values from the individual sensors in the group.

3. A system according to claim 1, further comprising that at least one temperature sensor is directly connected to the registration unit by means of its own cable.

4. A system according to claim 1, further comprising that the temperature sensors are provided with transmitters for wireless transfer of measurement values to a receiver at the registration unit.

5. A system according to claim 1 further comprising that the registration unit comprises a programmable processor for receiving and handling measurement values from the sensors.

6. A system according to claim 1 further comprising that the registration unit is connected to said computer unit, for processing and the analysis of received measurement values.

7. A system according to claim 1 further comprising that an alarm unit is connected to the system, in order to emit an alarm if a predetermined threshold condition is fulfilled.

8. A system according to claim 1 further comprising that the textile product is provided with one or more moisture sensors in order to register perspiration of the person.

9. A system according to claim 1 further comprising that the textile product is included in any of the following: a mattress, cushion or garment.

10. The system of claim 1, wherein said matrix of temperature sensors further comprises a plurality of rows and columns of temperature sensors, said temperature sensors numbering greater than two.

11. A method of monitoring the state of a person, comprising the steps of:
    providing a textile product intended to abut against the person during use, and being provided with a plurality of temperature sensors arranged to continuously measure the temperature of the person, wherein the temperature sensors are positioned in the textile product so as to form a matrix;
    providing a registration unit for registering measurement values from the temperature sensors;
    calculating (a) at least one spatial information parameter describing a distribution of a temperature over a surface covered by the sensors using a corresponding system of coordinates for analysing spatial temperature distribution, and (b) at least one temporal information parameter describing how said distribution of temperature has changed during a period of time;
    monitoring a predetermined threshold condition; and
    emitting an alarm signal to activate an alarm unit connected to the registering unit, when the condition is fulfilled.

12. The method of claim 11, wherein said matrix of temperature sensors further comprises a plurality of rows and columns of temperature sensors, said temperature sensors numbering greater than two.

13. A method of controlling characteristics of a foundation, based on the state of a person being present on the foundation, comprising the steps of:
    providing a textile product included in said foundation and intended to abut against the person during use, and being provided with a plurality of temperature sensors arranged to continuously measure the temperature of the person, wherein the temperature sensors are positioned in the textile product so as to form a matrix;
    providing a registration unit for registering measurement values from the temperature sensors;
    calculating (a) at least one spatial information parameter describing a distribution of a temperature over a surface covered by the sensors using a corresponding system of coordinates for analysing spatial temperature distribution, and (b) at least one temporal information parameter describing how said distribution of temperature has changed during a period of time; and
    controlling at least one physical characteristic of the foundation based on measurement values received from the temperature sensors.

14. A method according to claim 13, wherein the temperature is controlled in the foundation.

15. A method according to claim 14, wherein the temperature control in the foundation is further based on registered perspiration when one or more moisture sensors are used.

16. A method according to claim 13 wherein the pressure distribution at the surface of the foundation is analysed such that an excessive temperature at a certain spot or small area on the textile product during a certain time period indicates an excessive pressure as compared to the remaining surface, wherein the hardness of the surface or contact pressure is changed such that the pressure is relieved in said spot or area, in response to the excessive temperature.

17. The method of claim 13, wherein said matrix of temperature sensors further comprises a plurality of rows and columns of temperature sensors, said temperature sensors numbering greater than two.

* * * * *